United States Patent
Hanks

[11] Patent Number: 5,974,899
[45] Date of Patent: Nov. 2, 1999

[54] SOIL NUTRIENT EXTRACTION METHOD USING PRESSURIZED HOT WATER

[76] Inventor: Dallas A. Hanks, 1319 S. 1180 West, Orem, Utah 84058

[21] Appl. No.: 08/985,498

[22] Filed: Dec. 5, 1997

[51] Int. Cl.$^6$ .................................................. G01N 33/24
[52] U.S. Cl. ......................... 73/863.12; 73/866; 422/68.1
[58] Field of Search .................................. 73/863, 863.11, 73/863.12, 866; 422/68.1; 436/81, 79, 103, 110, 119

[56] References Cited

U.S. PATENT DOCUMENTS

| | | | |
|---|---|---|---|
| 5,526,705 | 6/1996 | Skotnikov et al. | 73/863 |
| 5,672,813 | 9/1997 | Doherty | 73/38 |

OTHER PUBLICATIONS

Hot water percolation (HWP): A new rapid soil extraction method Gy. Fuleky and I. Czinkota, Plant and Soil 157: 131–135, 1993.

Primary Examiner—Daniel S. Larkin
Attorney, Agent, or Firm—Madson & Metcalf

[57] ABSTRACT

An improved method of extracting nutrients from soil samples using hot water. The improved method utilizes an expresso coffee machine to force hot water through soil samples to which no filler materials such as silica sand has been added. Tests were performed with an expresso machine that generates a pressure of 2.5 bar and a temperature of 93° C. The method was performed with the following steps. Soils to be tested were air dried at a maximum temperature of 25° C. and passed through a 2.0 mm (number 10 mesh) screen. A 5.0-gram soil sample was placed in the expresso machine filter basket, which was lined with a 5.50-cm diameter medium filter paper. 100 ml of distilled water was placed in the expresso machine's boiler, and allowed to heat for 2.0 minutes. The heated water was released and passed through the soil sample until the boiler was empty and the filter basket without surface water. Extraction aliquots were allowed to cool. 10 ml samples from the extraction aliquots were tested for nitrate, phosphorus, sulfate, and potassium content, as well as for nitrate clarity and pH. Measured values correlated well with those obtained using standard nutrient extraction techniques.

20 Claims, 3 Drawing Sheets

SOIL NUTRIENT EXTRACTION METHOD USING PRESSURIZED HOT WATER

BACKGROUND OF THE INVENTION

1. Field of the Invention

This invention relates to soil nutrient extraction methods and, more particularly, to hot water nutrient extraction systems.

2. Description of Related Art

Increasing demand for soil analysis, prompted by environmental and economic factors, has intensified the need for an inexpensive, fast, convenient, and precise extraction method. Wet chemistry extractions for soil analyses are often labor intensive, complicated or environmentally hazardous. The extractions are generally tedious, typically involve expensive equipment, require considerable laboratory space, and normally involve the use of numerous chemical reagents. These factors render contemporary soil analysis methods prohibitively expensive for all but the most serious agronomic and horticultural pursuits. Simplified soil analysis procedures, if commercially available, are unlikely to extract multiple nutrients in one step and generally require varied reagent use for extractions.

The search for a simple, one-step, nutrient extraction method utilizing hot water was probably initiated early in the twentieth century by Konig (1906). Anion exchange resin, in combination with water, has been used to measure the total desorption of phosphorus (Amer, et al., 1955). Van der Paauw (1969) proposed that phosphorus (P) extraction efficiency could be improved by using a soil-water ratio of 1:50. Korschens, et al. (1984) used the Soxhlet extraction technique, which utilizes water, to extract and measure carbon (C) and nitrogen (N) in soils. Suntheim and Matzel (1985) used a continuous water extraction technique to determine phosphorus conent in soils. Most recently, a hot water percolation method to extract both macro and micro nutrients was reported for acidic soils of Hungary by Fulkey and Czinkota (1993). Using this method, a mixture consisting of a 30 g soil sample and 10 g of sand was placed on the filter of a coffee percolator and water preheated to 102–105° C. was percolated through the sample under a pressure of 120 to 150 kilopascals (equivalent to about 1.2 to 1.5 bar or 17.4 to 21.75 lbs./in$^2$) until about 100 to 500 ml of extract were collected. Results obtained from this latter extraction process compared favorably with plant uptake experiments for acidic soils. Fulkey and Czinkota determined that the time required to obtain 100 ml of extract for percolation through pure soil samples averaged 41 minutes, while an average of 188 minutes was required to obtain 500 ml of extract. Because of such unreasonably long percolation times, they determined that it was necessary to dilute the soil samples with sand. They determined that too much sand resulted in such rapid percolation that the amount of nutrients released into the accumulated extract was insufficient for accurate quantitative analysis of the soil sample. Through trial and error, it was determined that a mixture of 25% sand and 75% soil sample, by weight, provided the best combination of reasonable percolation times (an average of 2.6 minutes for 100 ml of extract) and adequate release of nutrients into the extract.

What is needed is an improved method for hot water extraction of nutrients from soil samples which is inexpensive, rapidly performed, capable of providing excellent analytical results for a variety of nutrients, and which does not require the mixing of sand with a soil sample. Ideally, such an improved method would make use of readily available equipment which could be used, without modification, to practice the improved method, or which could be readily and inexpensively modified for such practice.

SUMMARY OF THE INVENTION

The invention fills the heretofore expressed need for an improved method of extracting nutrients from soil samples using hot water. The improved method utilizes an expresso coffee machine to force hot water through soil samples to which no filler materials such as silica sand had been added. Tests were performed with a Braun model E-250T expresso machine supplied by Braun, Inc., Lynnfield, Mass.). The E-250T generates a pressure of 2.5 bar and a temperature of 93° C.

The method was performed with the following steps. Soils to be tested were air dried at a maximum temperature of 25° C. and passed through a 2.0 mm (number 10 mesh) screen. A 5.0-gram soil sample was placed in the expresso machine filter basket, which was lined with a 5.50-cm diameter medium filter paper. 100 ml of distilled water was placed in the expresso machine's boiler, and allowed to heat for 2.0 minutes. The heated water was released and passed through the soil sample until the boiler was empty and the filter basket without surface water. This generally occurred in 0.5 to 5 minutes. Extraction aliquots were allowed to cool and the volumes measured ranged from 64 to 91 ml and averaged 79 ml. 10 ml samples from the extraction aliquots were tested for various soil nutrients. Nitrate ($NO_3$) content was quantified calorimetrically by using a chromatropic acid procedure according to Sims and Jackson (1971). Clarity of the sample for nitrate was determined by adding 0.35 grams of $Ca(OH)_2$ to a 10 ml sample, the mixture was shaken for 5 seconds, centrifuged at 2,000 RPM for 45 seconds, and the resultant solution used in nitrate analysis. Sulfate ($SO_4$) content was determined using an ion chromatograph. Potassium (K) content was analyzed using an atomic absorption spectrophotometer. The pH value for the sample was determined with a conventional pH meter. Phosphorus (P) content was determined calorimetrically using a molybdenum-blue procedure according to Watanabie and Olsen (1965).

For comparison and calibration purposes, the same soils analyzed using the new hot water extraction method were also analyzed for nitrate content, sulfate content, potassium content, phosphorus content and pH using widely-recognized standard methods. The procedures used are hereinafter identified. Linear regression analysis was employed to predict the relationship between the nutrient values obtained using the new hot water method and the nutrient values obtained via the standard nutrient analysis procedures.

PREFERRED EMBODIMENT OF THE INVENTION

Figure 1:
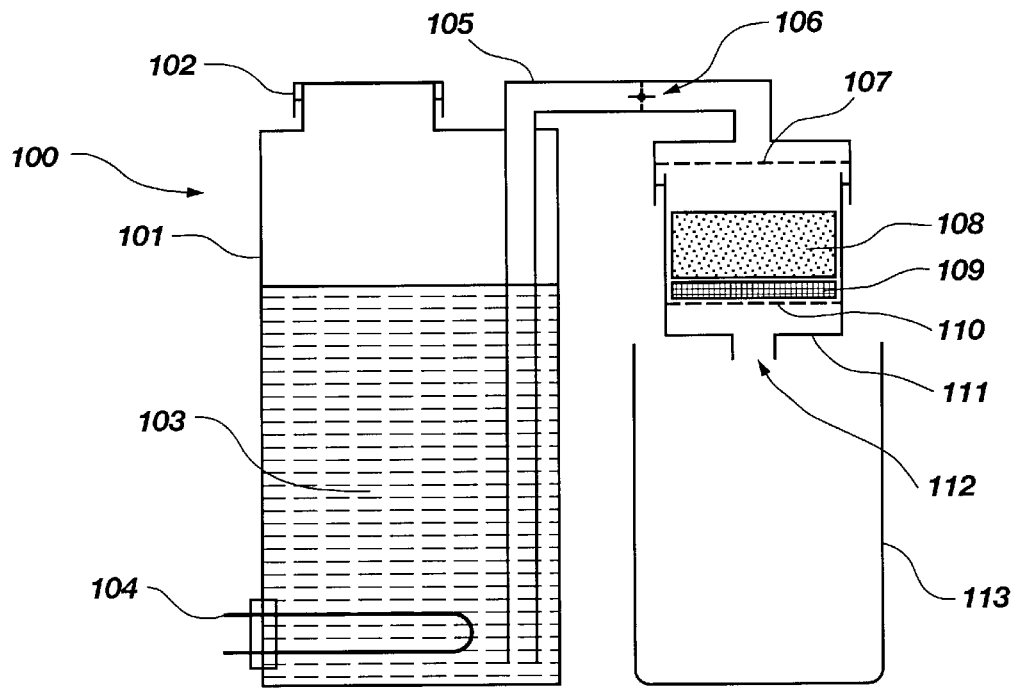
FIG. 1 is a schematic diagram of the apparatus used to practice the soil nutrient extraction method of the present invention.

Hot water extraction has been shown to be an effective method for determining the amounts of various important nutrients present in soil samples. In addition, the derived analytical results have been shown to correlate favorably with those obtained using conventional soil analysis methods. This invention provides a rapid and greatly simplified method for performing hot water extraction of soil nutrients. The improved method utilizes a high-pressure nutrient extraction apparatus, such as an expresso coffee machine, to force hot water through soil samples.

For comparison and calibration purposes, thirty-eight different arid-zone soil samples were analyzed for texture, nutrient content and pH using widely-recognized standard methods. Nitrate content was determined via a procedure developed by Kowalenko and Lowe (1973); sulfate content via a procedure devised by Williams and Stanley (1962); potassium content via a procedure recognized by the Council on Soil Testing and Plant Analysis (1980); phosphorus content via a procedure developed by Watanabe and Olsen (1965); and pH using a standard saturated paste method devised by Richards (1954). Extractions were replicated three times with a randomized complete block design. The results from the new hot water method and the standard extraction procedures were correlated using a technique developed by Goulden (1952). Linear regression analysis was employed to predict the relationship between the nutrient values obtained using the new hot water method and the nutrient values obtained via the standard nutrient analysis procedures. The following Table 1 provides the results of the standard method analyses.

TABLE 1

| Sand | Silt | Clay | Texture | $NO_3$ | P | K | $SO_4$ | pH |
|------|------|------|---------|--------|---|---|--------|-----|
| percent by weight | | | | | mg kg$^{-1}$ | | | |
| 22.9 | 30.9 | 46.2 | clay loam | 17.7 | 35.3 | 246.4 | * | * |
| N/A | N/A | N/A | N/A | 17.8 | 50.2 | 320.0 | * | * |
| 20.9 | 28.9 | 50.2 | clay loam | 47.8 | 33.4 | 192.0 | * | * |
| N/A | N/A | N/A | N/A | 6.6 | 12.0 | 403.2 | * | * |
| N/A | N/A | N/A | N/A | 35.5 | 94.8 | 137.6 | * | * |
| 70.6 | 12.9 | 16.5 | sandy loam | 48.2 | 103.3 | 131.2 | * | * |
| 64.6 | 12.9 | 22.5 | sandy loam | 5.2 | 10.9 | 105.6 | * | * |
| 20.6 | 38.9 | 40.5 | clay loam | 9.1 | 14.3 | 387.2 | * | * |
| 50.6 | 32.9 | 16.5 | sandy clay loam | 4.2 | 17.0 | 246.4 | * | * |
| 41.5 | 30.9 | 27.6 | clay loam | 9.9 | 29.7 | 172.8 | * | * |
| 38.2 | 28.9 | 32.9 | clay loam | 5.5 | 23.7 | 243.2 | * | * |
| 32.2 | 38.9 | 28.9 | clay loam | 5.8 | 11.0 | 256.0 | * | * |
| 50.2 | 28.9 | 20.9 | sandy clay loam | 4.6 | 12.6 | 291.2 | * | * |
| 38.5 | 26.9 | 34.5 | clay loam | 6.6 | 50.9 | 1052.8 | * | * |
| 32.2 | 32.9 | 34.9 | clay loam | 9.7 | 15.7 | 112.0 | * | * |
| 40.6 | 28.9 | 30.5 | clay loam | 22.6 | 10.3 | 342.4 | * | * |
| 38.6 | 28.9 | 32.5 | clay loam | 8.19 | 7.6 | 67.2 | * | * |
| 40.6 | 28.9 | 30.5 | clay loam | 18.9 | 32.0 | 54.4 | * | * |
| 39.9 | 11.0 | 49.1 | loam | 6.1 | 36.2 | 346.7 | * | * |
| 65.6 | 25.0 | 9.4 | sandy clay loam | 6.0 | 7.0 | 58.7 | 2.0 | 6.8 |
| 88.0 | 4.7 | 7.4 | sand | 10.3 | 19.4 | 316.8 | 3.4 | 7.5 |
| 26.6 | 28.7 | 44.7 | clay loam | 41.4 | 37.4 | 316.8 | 42.1 | 8.1 |
| 54.6 | 30.3 | 15.1 | sandy clay loam | 21.7 | 42.6 | 304.0 | 76.0 | 7.7 |
| 42.6 | 30.3 | 27.1 | clay loam | 58.2 | 30.4 | 406.6 | 158.6 | 7.5 |
| 20.6 | 26.3 | 53.1 | silty clay loam | 3.9 | 7.4 | 60.8 | 0.7 | 6.4 |
| 20.6 | 26.3 | 53.1 | clay | 17.7 | 11.3 | 145.1 | 36.6 | 6.5 |
| 74.2 | 23.7 | 2.1 | sandy clay loam | 3.5 | 10.4 | 88.5 | 3.3 | 6.5 |
| 38.9 | 20.4 | 40.7 | loam | 2.9 | 54.4 | 150.4 | 7.1 | 7.0 |
| 30.6 | 10.7 | 58.7 | silt loam | 30.3 | 49.5 | 232.5 | 27.7 | 7.6 |
| 38.2 | 38.7 | 23.1 | clay loam | 15.1 | 65.8 | 205.9 | 13.9 | 6.8 |
| 37.5 | 18.7 | 43.8 | loam | 19.8 | 33.4 | 330.7 | 20.9 | 7.0 |
| 25.2 | 38.7 | 36.0 | clay loam | 17.6 | 40.7 | 203.7 | 22.5 | 7.5 |
| 22.2 | 38.0 | 39.8 | clay loam | 17.0 | 20.1 | 165.3 | 18.6 | 7.6 |
| 38.2 | 53.7 | 8.0 | clay | 24.0 | 9.7 | 352.0 | 4.9 | 7.2 |
| 26.2 | 28.3 | 45.4 | clay loam | 36.1 | 88.0 | 295.5 | 50.7 | 7.6 |
| 22.2 | 25.3 | 52.4 | silt loam | 15.9 | 17.0 | 195.2 | 10.3 | 7.4 |
| 46.9 | 19.0 | 34.1 | loam | 18.4 | 6.7 | 624.0 | 12.7 | 8.2 |
| 40.6 | 26.4 | 33.1 | loam | 155.8 | 22.0 | 196.3 | 90.5 | 7.1 |

N/A: Remnants of samples were not large enough for textural analysis.
*: These soils were not included in study on pH and sulfate.

FIG. 1 depicts a schematic diagram of a high-pressure extraction apparatus 100 employed in conjunction with the new hot water nutrient extraction method. The Braun model E-250T expresso machine, supplied by Braun, Inc. of Lynnfield, Mass. is one such apparatus that is suitable for use with the new hot water nutrient extraction method. The E-250T generates water pressure of 2.5 bar and a temperature of 93° C. Referring now to FIG. 1, a pressure chamber 101 is sealably capped with a removable lid 102 after being filled with distilled water 103. A heating coil 104 heats the water 103 to near boiling temperature. A pressure tube 105 interconnects the pressure chamber with a sample holder 111 that is sealably connected to the pressure tube 105. Valve 106 is maintained in a closed position until the water 103 reaches the desired temperature. Within a temperature range of 90 to 100° C., the most significant soil nutrients are sufficiently soluble to enable accurate analysis using conventional techniques. However, as temperatures beyond this range will provide increased solubility of nutrients, the method may be employed, at least theoretically, at temperatures below which nutrient decomposition begins to take place. As a practical matter, though, temperatures near and above boiling pose at least some risk of burning and scalding to the individual performing the extraction. In addition, energy is wasted by heating the water beyond temperatures required for accurate analysis. At pressures of much less than 2.0 bar, the time required to complete the extraction process becomes inconveniently long unless a filler material such as sand is added to the sample. The sample holder 111 has a perforated sample support plate 110. A medium filter paper 109 is placed directly on the support plate 110, and the soil sample 108 is placed on top of the filter paper 109. When the valve 106 is opened after optimum water temperature is achieved, the water flows from the pressure vessel 103 through pressure tube 105, through the diffuser plate 107, through the soil sample 108, through the filter paper 109, through the perforated support plate, through the escape opening 112 and into a collection flask 113. The hot water passed through the soil samples is collected and analyzed. The method utilizes air-dried soil samples to which no filler materials such as silica sand have been added.

Soil nutrient analysis for the same 38 samples was then performed via the new hot water method using the following steps. Each soil sample was air dried at a maximum temperature of 25° C. and passed through a 2.0 mm (number 10 mesh) screen. A 5.0-gram mass of each sample was then placed in the expresso machine filter basket, which was lined with a 5.50-cm diameter medium filter paper. 100 ml of distilled water was placed in the expresso machine's boiler, and allowed to heat for 2.0 minutes. The heated water was released and passed through the 5.0-gram sample until the boiler was empty and the filter basket without surface water. This generally occurred in 0.5 to 5 minutes. Extraction aliquots were allowed to cool and the volumes measured ranged from 64 to 91 ml and averaged 79 ml. 10 ml samples from the extraction aliquots were tested for various soil nutrients. Nitrate ($NO_3$) content was quantified calorimetrically by using a chromatropic acid procedure according to Sims and Jackson (1971). Clarity of the sample for nitrate was determined by adding 0.35 grams of $Ca(OH)_2$ to a 10 ml sample, the mixture was shaken for 5 seconds, centrifuged at 2,000 RPM for 45 seconds, and the resultant solution used in nitrate analysis. Sulfate ($SO_4$) content was determined using an ion chromatograph. Potassium (K) content was analyzed using an atomic absorption spectrophotometer. The pH value for the sample was determined with a conventional pH meter. Phosphorus (P) content was determined colorimetrically using a molybdenum-blue procedure according to Watanabie and Olsen (1965).

As depicted by Table 1, the 38 different soils tested were diverse in pH, texture and nutrient content. One step extraction with hot water provided measurable quantities of $NO_3$, $SO_4$, K, and P in all 38 calcareous soils tested. The correlation coefficient (r) of hot water extractions with standard methods ranged from 0.99 to 0.60. Resulting regression equations and statistically significant coefficients of determination allow conversion to "standard" values for interpretation.

Nitrate values for the 38 soils using standard extraction methods ranged from 4 to 233 mg-kg$^{-1}$ (Table 1) and from 3 to 156 mg-kg$^{-1}$ nitrate nitrogen using the new hot water extraction method (FIG. 1). The relationship between the hot water method and the standard methods was excellent [$r^2=0.98(p=0.001)$]. Thus, effective removal of nitrate was achieved with the new extraction method. These results are not surprising given the high water solubility of nitrate.

Figure 2:
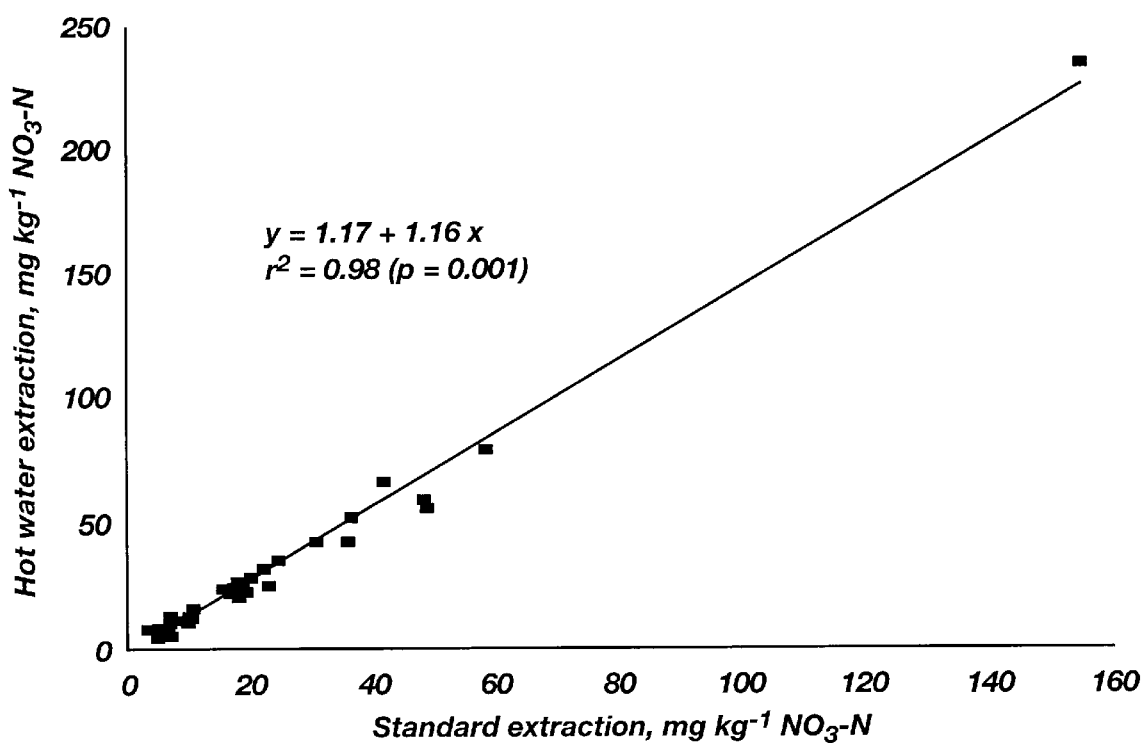
FIG. 2 is a graph of the predicted relationship between nitrate nitrogen extracted from 38 arid-zone soils by hot water and standard extraction methods.
Figure 3:
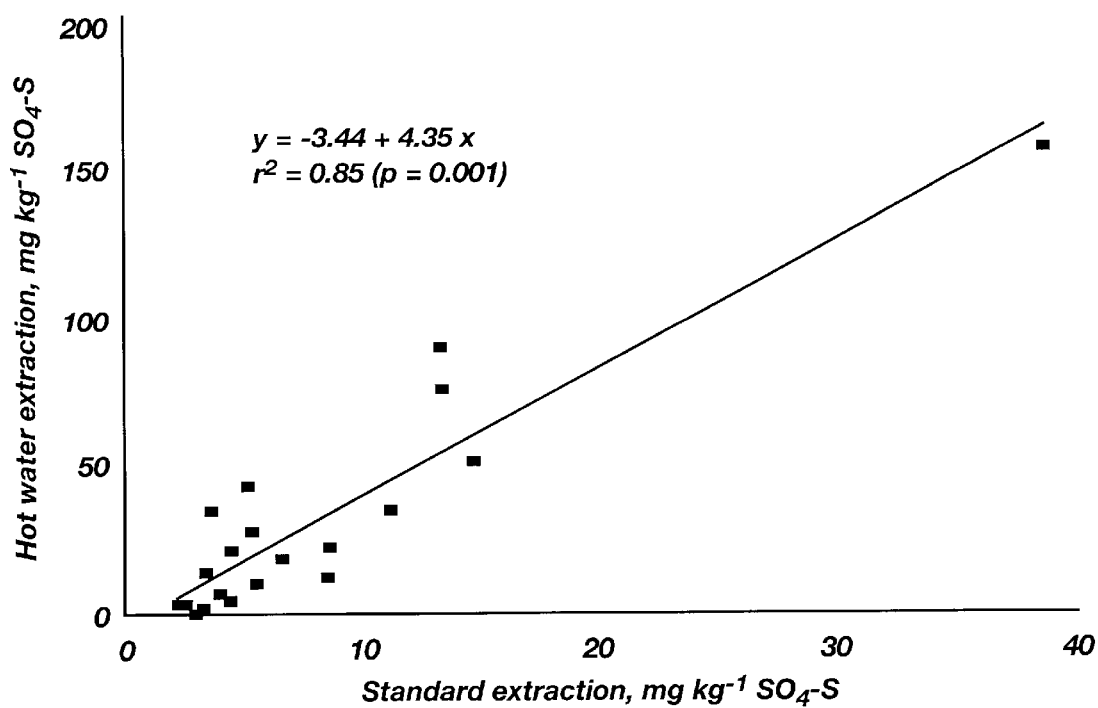
FIG. 3 is a graph of the predicted relationship between sulfate sulfur extracted from 20 arid-zone soils by hot water and standard extraction methods.

Sulfate values for the twenty soils tested using standard extraction methods ranged from 2 to 159 mg-kg$^{-1}$ (Table 1) and from 2 to 39 mg-kg$^{-1}$ sulfate sulfur using the new hot water extraction method (FIG. 2). Extraction values from the two techniques were closely related [$r^2=0.85(p=0.001)$] (FIG. 2). As for nitrate, the high water solubility of sulfate would suggest that a close correlation would be found.

Potassium values for the 38 soils using standard extraction methods ranged from 54 to 1,053 mg-kg$^{-1}$ (Table 1) and from 26 to 522 mg-kg$^{-1}$ using the new hot water method. The coefficient of determination for the regression equation comparing the two techniques was [$r^2=0.72(p=0.001)$]. As potassium levels approached 400 mg-kg$^{-1}$ (values well above the critical concentrations for the recommendation of fertilizer), the new hot water technique was unable to extract as effectively as the standard method.

Figure 4:
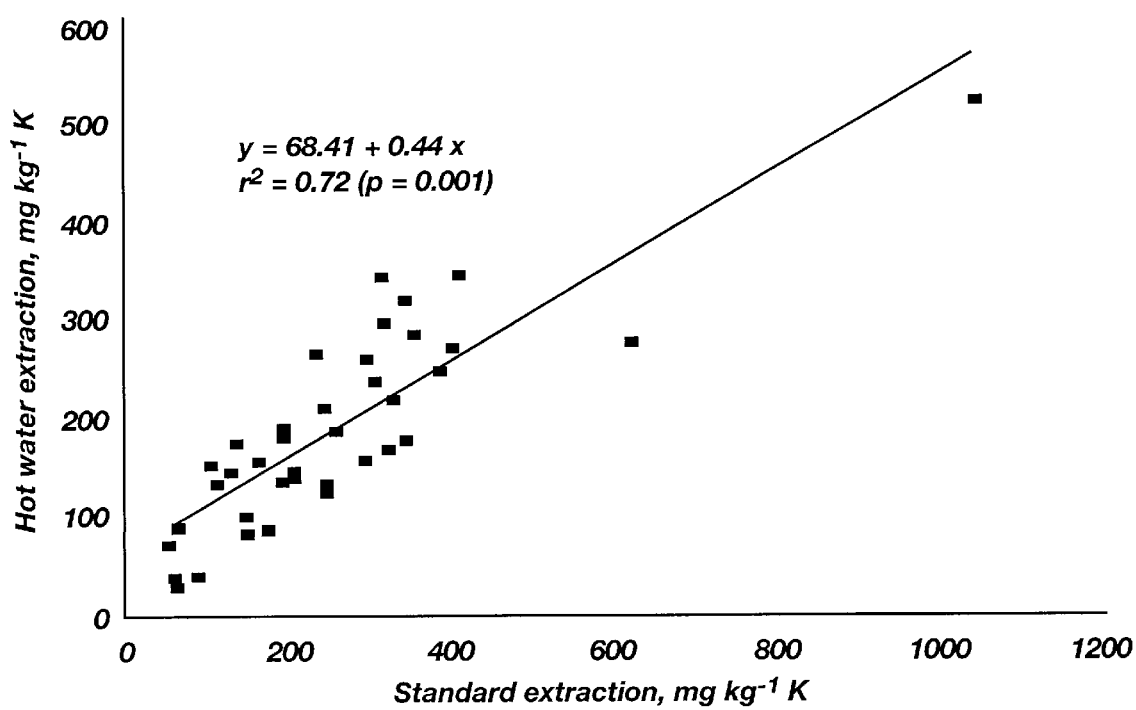
FIG. 4 is a graph of the predicted relationship between potassium extracted from 38 arid-zone soils by hot water and standard extraction methods.

Phosphorus values determined using standard methods ranged from 7 to 103 mg-kg$^{-1}$ (Table 1) and from 1 to 47 mg-kg$^{-1}$ phosphate phosphorus using the new hot water extraction method (FIG. 4). Expectedly, phosphate levels determined with the hot water method were lower than with the standard method. However, the correlation between the values obtained using the hot water method and those obtained using the standard method was significant [$r^2=0.35(p=0.001)$].

Phosphorus content in western soils is traditionally regarded as being tightly held in a calcium phosphate complex which makes extraction difficult using hot water. Thus, the significant relationship observed was a surprise. The relationship can probably be improved by, for example, increasing either, or possibly both, the temperature and pressure of the water, or by changing the water to soil ratio used in the extraction process.

Figure 5:
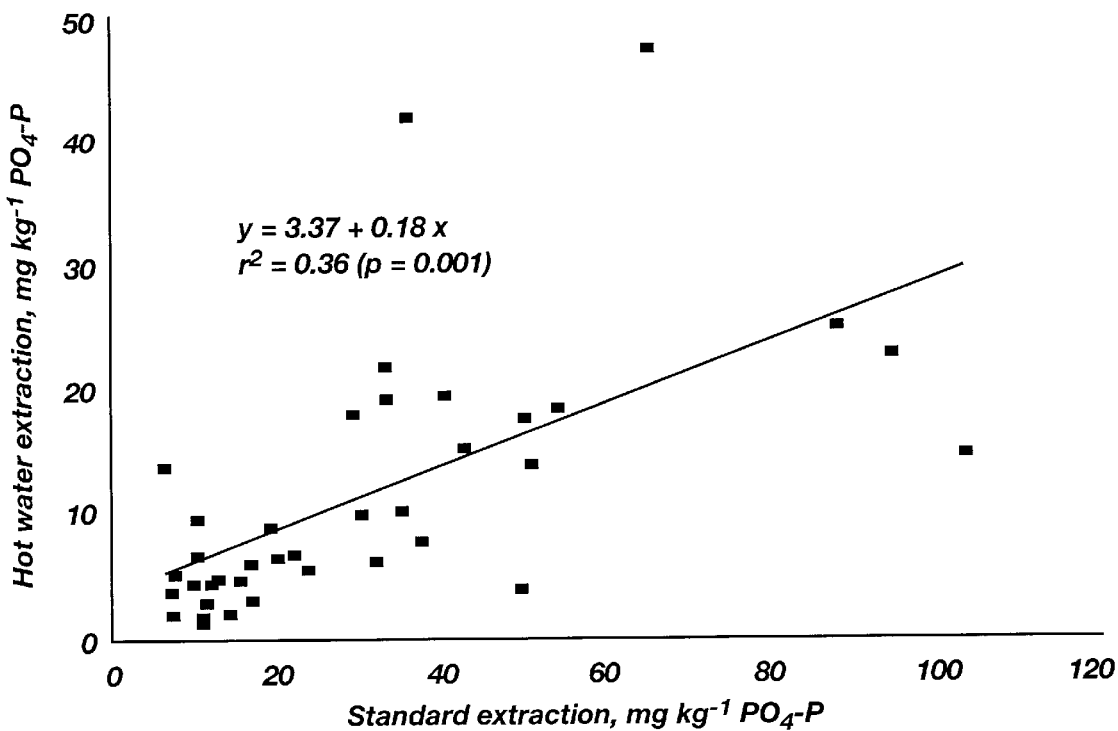
FIG. 5 is a graph of the predicted relationship between phosphate phosphorus extracted from 38 arid-zone soils by hot water and standard extraction methods.
Figure 6:
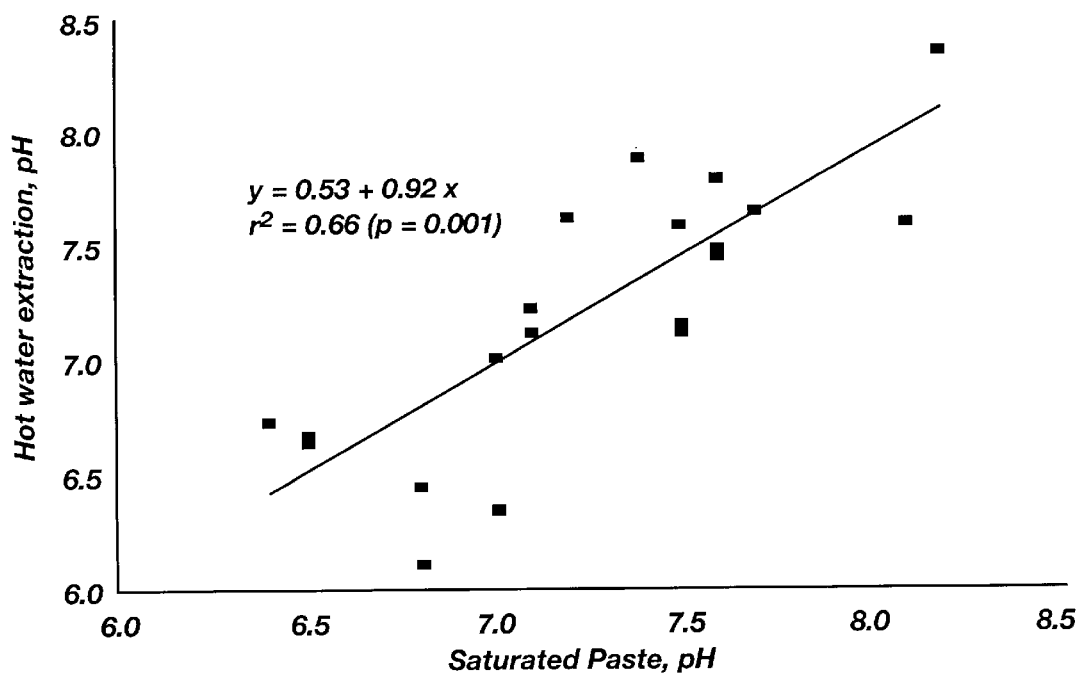
FIG. 6 is a graph of the predicted relationship between pH of 20 arid-zone soils measured on a saturated paste and on the hot water extract.

The pH on saturated pastes for the 20 soils tested ranged from 6.4 to 8.2 (Table 1) and, using the new hot water extraction method, from 6.1 to 8.3 (FIG. 5). Values from the two techniques were predictably related [$r^2=0.67(p=0.001)$]. Thus, extractions using the new hot water method are adequate to measure pH in alkaline soils.

From the above results, it can be readily observed that the new hot water extraction method is effective for measuring nitrate, phosphate, sulfate, potassium, and pH. The method provides good correlation to standard extraction procedures in alkaline soils, thus allowing easy conversion of hot water extraction values to standard values. It should be emphasized that the correlations derived from the results obtained in the experiments discussed herein are valid for water temperatures of 93° C. and for extraction aliquots obtained starting with 100 ml of water. Variations from these parameters will require recalibration of the results obtained. The new method can be performed rapidly with no chemical extractants and requires no dilution of the soil sample with a filler such as silica sand. The equipment used for the new extraction method is commercially available, simple to use and relatively inexpensive. The use of hot water for the extraction process reduces the dependence on chemicals used in standard extractions.

Although only a single embodiment of the new hot water soil nutrient extraction method is described herein, it will be obvious to those having ordinary skill in the art that changes and modifications may be made thereto without departing from the scope and the spirit of the invention as hereinafter claimed.

What is claimed is:

1. A method for extracting nutrients from a soil sample comprising the steps of:

passing water heated to a temperature of at least 90° C. through the sample under a pressure of at least 2.0 bar; and collecting the water passed through the sample so that any nutrients transferred from the soil to the water may be subsequently analyzed.

2. The method of claim 1, wherein said sample has a weight of about five grams.

3. The method of claim 1, wherein the method for extracting nutrients is completed in less than 5 minutes.

4. The method of claim 1, which further comprises the step of passing the sample through a screen having a uniformly sized mesh.

5. The method of claim 4, wherein a screen having a 2 mm (#10) mesh is utilized.

6. The method of claim 1, wherein the water is also passed through filter paper on which the sample is placed.

7. The method of claim 1, wherein the soil sample is unadulterated with a non-compacting filler material.

8. The method of claim 1, wherein the step of passing water heated to a temperature of at least 90° C. through the sample under a pressure of at least 2.0 bar is performed using an expresso machine.

9. A method for extracting nutrients from a soil sample unadulterated with a non-compacting filler material comprising the steps of:

passing water heated to at least about 93° C. through the sample under a pressure of at least about 2.5 bar; and collecting the water passed through the sample for subsequent nutrient analysis.

10. The method of claim 9, wherein said sample is dried prior to extracting nutrients.

11. The method of claim 9, which further comprises the step of passing the sample through a screen having a uniformly sized mesh.

12. The method of claim 9, wherein a screen having a 2 mm (#10) mesh is utilized.

13. The method of claim 9, wherein the water is also passed through filter paper on which the sample is placed.

14. The method of claim 9, wherein the step of passing water heated to a temperature of at least 90° C. through the sample under a pressure of at least 2.0 bar is performed using an expresso machine.

15. The method of claim 9, wherein said sample has a weight of about 5 grams.

16. A method for extracting nutrients from a soil sample comprising the steps of:

obtaining about 5 grams of soil sample;

passing water heated within a range of 90 to 100° C. through the sample under a pressure of at least 2.0 bar; and collecting the water passed through the sample for subsequent nutrient analysis.

17. The method of claim 16, wherein the method for extracting nutrients is completed in less than 5 minutes.

18. The method of claim 16, which further comprises the step of passing the sample through a screen having a uniformly sized mesh.

19. The method of claim 16, wherein a screen having a 2 mm (#10) mesh is utilized.

20. The method of claim 16, wherein the water is also passed through filter paper on which the sample is placed.

* * * * *